(12) United States Patent
Hwang et al.

(10) Patent No.: US 7,417,172 B2
(45) Date of Patent: Aug. 26, 2008

(54) PERFLUOROALKYL VINYL ETHER COMPOUND, PROCESS FOR PREPARING COPOLYMER BY USING THE COMPOUND, AND OPTICAL PLASTIC MATERIALS COMPRISING COPOLYMER PREPARED BY THE PROCESS

(75) Inventors: Jin Taek Hwang, Daejeon-Si (KR); Do Yoon Kim, Daejeon-Si (KR); Jin Sung Choi, Gyeonggi-Do (KR); Boris Maximov, St. Petersburg (RU); Victor Sergeevich Yuminov, St. Petersburg (RU); Lev Feodorovich Sokolov, St. Petersburg (RU)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 326 days.

(21) Appl. No.: 10/864,490

(22) Filed: Jun. 10, 2004

(65) Prior Publication Data

US 2005/0148800 A1    Jul. 7, 2005

(30) Foreign Application Priority Data

Jan. 6, 2004    (KR)    ............ 10-2004-0000529

(51) Int. Cl.
*C07C 43/166*    (2006.01)

(52) U.S. Cl. ..................... 568/663; 568/662

(58) Field of Classification Search ............ 568/669, 568/663
See application file for complete search history.

(56) References Cited

U.S. PATENT DOCUMENTS

| 3,467,638 | A  | * | 9/1969 | Pottison | 526/247 |
| RE29,534 | E | * | 2/1978 | Resnick | 260/543 F |
| 4,140,699 | A | * | 2/1979 | Martini | 549/378 |
| 6,255,536 | B1 | * | 7/2001 | Worm et al. | 568/615 |

FOREIGN PATENT DOCUMENTS

| EP | 0 626 352 A2 | 11/1994 |
| JP | 8-334634 | 12/1996 |
| JP | 10-2168146 | 10/1998 |

OTHER PUBLICATIONS

CA Absract for Yuminov , Zhurnal Organicheskoi Khimii, 1995, vol. 31(8), pp. 1145-1148.*
Hill, J. T., Octafluoroisobutylene epoxide derivatives, Journal of Fluorine Chemistry, Feb. 1977, vol. 9, Issue 2, abstract.*

* cited by examiner

*Primary Examiner*—Rosalynd Keys
(74) *Attorney, Agent, or Firm*—Buchanan Ingersoll & Rooney PC

(57) ABSTRACT

A novel perfluoroalkyl vinyl ether compound, a process for preparing a copolymer by using the perfluoroalkyl vinyl ether compound, and an optical plastic material comprising a copolymer prepared by the process are provided. More specifically, the perfluoroalkyl vinyl ether has a particular molecular structure; the process is performed by copolymerizing the perfluoroalkyl vinyl ether compound with a common fluorinated olefin in the presence of a perfluorinated radical initiator; and the optical plastic material comprises a copolymer prepared by the process and optionally a dopant.

1 Claim, 2 Drawing Sheets 1. polymerization ampoule
2. thermos bottle filled with liquid nitrogen
3. trap cooled with liquid nitrogen
4. rubber ball filled with argon
5. ultra-thermostat 1. reactor
2. heating jacket
3. thermocouple
4. TFE cylinder
5. TFE cylinder(buffer)
6. Absorber (TFE purification)
7. agitator

PERFLUOROALKYL VINYL ETHER COMPOUND, PROCESS FOR PREPARING COPOLYMER BY USING THE COMPOUND, AND OPTICAL PLASTIC MATERIALS COMPRISING COPOLYMER PREPARED BY THE PROCESS

BACKGROUND OF THE INVENTION

This non-provisional application claims priority under 35 U.S.C. § 119(a) to Korean Patent Application No. 2004-529 filed on Jan. 6, 2004, which is herein incorporated by reference.

FIELD OF THE INVENTION

The present invention relates to a novel perfluoroalkyl vinyl ether compound, a process for preparing a copolymer by using the perfluoroalkyl vinyl ether compound, and an optical plastic material comprising a copolymer prepared by the process. More particularly, the present invention relates to a cyclic perfluoroalkyl vinyl ether having a particular molecular structure, a process for preparing a copolymer by copolymerizing the perfluoroalkyl vinyl ether compound with a common fluorinated olefin in the presence of a perfluorinated radical initiator, and an optical plastic material comprising a copolymer prepared by the process, and optionally a dopant.

DESCRIPTION OF THE RELATED ART

In recent years, a number of optical plastic materials have been used as media for light transmission in the field of automobiles, OA machines and various sensors. For example, plastic optical fibers (POFs) are widely used as optical fibers for short-distance communication in place of quartz glass. Plastic optical fibers are largely classified into graded refractive index (GI) type POFs and stepped refractive index (SI) type POFs. Generally, methylmethacrylate, styrene, carbonate, norbornene resins and the like are used as cores or clads of optical fibers. These resins are polymers having C—H bonds in their molecular structure. When the polymer materials are used as materials for optical fibers, stretching or deformation vibration takes place due to the presence of hydrogen atoms in the C—H bonds. As a result, the polymer materials absorb light of a characteristic wavelength corresponding to the vibration and light transmittance is therefore decreased. This is a main cause of optical loss. For instance, polymethylmethacrylate is evaluated to have a theoretical absorption loss of 105 dB/km for a 650 nm light source and 10,000 dB/km for a 1,300 nm light source, due to C—H bonds contained in the compound.

It has been found that when the hydrogen atoms in the polymers are replaced with fluorine atoms, no absorption loss substantially takes place for a 650 nm light source and a theoretical absorption loss is only about 1 dB/km between sixth and seventh overtones of the C—F bonds for a 1,300 nm light source. For this reason, extensive research has been undertaken on the use of fluorine polymers having C—F bonds as materials for optical fibers.

For example, Japanese Patent Laid-open No. Hei 8-334634 discloses poly(heptafluoro-1-butene-trifluoro-vinylether) (hereinafter, referred to as 'PBVE'), as a completely fluorinated optical plastic material, represented by the following formula:

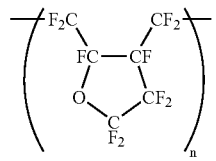

This polymer is prepared by homopolymerizing perfluoro-(2,2-dimethyl-1,3-dioxole) having an allyl cyclic structure containing fluorine atoms in the main chain of the monomer, or copolymerizing the monomer with tetrafluoroethylene or hexa-fluoropropylene.

Since the polymer PBVE is prepared from the monomer having an allyl cyclic structure containing fluorine atoms in the main chain, it contains no C—H bonds. In addition, it is known that PBVE has an amorphous structure and a $T_g$ of 108° C. Further, the polymer PBVE is commercially available under the brand name of "CYTOP" from Asahi Glass Co., Japan.

In addition to PBVE, Asahi Glass Co. proposed fluorinated polymers as materials for a GI (graded index) plastic optical fiber, represented by the following formulae:

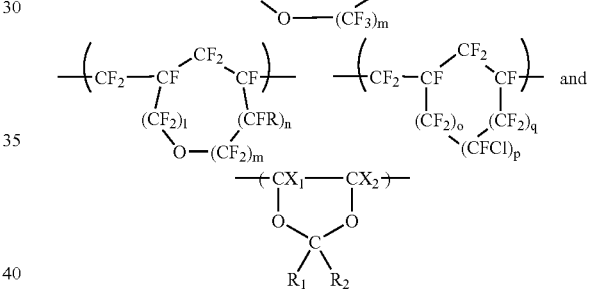

wherein l is a number of 0 to 5, m is a number of 0 to 4, n is a number of 0 to 1, and l+m+n is a number of 1 to 6; o, p and q are each independently a number of 0 to 5, and o+p+q is a number of 1 to 6; R, $R_1$ and $R_2$ are each independently F or $CF_3$; and $X_1$ and $X_2$ are each independently F or Cl.

In order to produce POFs, particularly GI type POFs having a refractive index gradient using the above perfluorinated polymers, the use of dopants is required (e.g., low molecular weight compounds or high molecular weight compounds of oligomers or higher polymers containing no C—H bonds in their molecular structure). Additional requirements for the dopants are excellent compatibility with host polymers and a refractive index difference from the host polymers above a predetermined level. Many low molecular weight dopants are known, for example, halogenated aromatic hydrocarbons containing no C—H bonds. Among these hydrocarbons, halogenated aromatic hydrocarbons containing only fluorine atoms as halogen atoms and halogenated aromatic hydrocarbons containing fluorine atoms and other halogen atoms are preferred in terms of high compatibility with host polymers. As high molecular weight or oligomeric dopants, perfluorinated polymers having a refractive index different from host polymers are known, for example, perfluorinated polymers containing only fluorine atoms as halogen atoms, and perfluorinated polymers containing fluorine atoms and other halogen atoms.

The production of GI type POFs using a perfluorinated polymer such as CYTOP is achieved by first fabricating a preform for a plastic optical fiber (POF) having a refractive index gradient in a polymer by using a dopant, followed by thermal drawing. At this time, the fabrication of the preform is possible by various methods (see, e.g., Japanese Patent Nos. 10-268146 and Japanese Patent Laid-open No, Hei 8-334534): For example, 1) A perfluorinated polymer is melted; a dopant or a perfluorinated polymer containing the dopant is fed into the central portion of the molten polymer; and, the dopant is diffused so as to be molded into a preform.

2) A perfluorinated polymer prepared by melt-spinning; drawing is used to form a central rod; and a dopant or a perfluorinated polymer containing the dopant is repeatedly dip-coated onto the rod.

3) A hallow is formed in a perfluorinated polymer using a rotating glass tube; a dopant or a perfluorinated polymer containing the dopant is filled into the perfluorinated polymer tube; and, the resulting structure is rotated at a low speed.

4) A homogeneous mixture of a perfluorinated polymer and a dopant—or a mixture obtained by uniformly mixing the perfluorinated polymer and the dopant in a solvent and evaporating the solvent only—is thermally drawn or melt-extruded to produce a fiber; and, the fiber is contacted with an inert gas under heating to form a refractive index gradient.

5) A rod or fiber consisting of a perfluorinated polymer is formed; a dopant having a refractive index lower than the perfluorinated polymer or a perfluorinated polymer containing the dopant is coated on the rod or fiber; and, the coated structure is heated to diffuse the dopant, thereby forming a refractive index gradient.

6) A high refractive index polymer and a low refractive index polymer at various mixing proportions are heat-melted or mixed in a solvent; and the obtained mixtures are diffused by extruding in a multilayer, thereby producing a fiber having a refractive index gradient.

7) A stepped or multi-stepped preform is fabricated using a perfluorinated polymer and a dopant, and the dopant is diffused at the interface between the steps to produce a GI type optical fiber.

In accordance with the above-mentioned methods, Asahi Glass Co., Japan and professor Koike developed GI type POF (commercial name: "Lucina") having excellent optical properties at the level of an attenuation of 80 dB/km and a bandwidth of 3 Gbps/100 m. It was developed so as to apply to office LAN and optical interconnection. "Lucina" exhibits a very low optical loss, a large transmission capacity at various wavelengths, and excellent moisture resistance. However, the present inventors have found problems with "Lucina" in that the optical properties are non-uniform along the length of the fiber, and the dopant used to control the refractive index gradient acts as a plasticizer. This greatly deteriorates the thermal properties of the base resin, damaging the long-term reliability. Particularly, the refractive index gradient is deformed, decreasing the transmission capacity.

Accordingly, prior art perfluorinated polymers are not suitable to produce POFs for access networks, office networks, automobiles, military purposes and aircraft, which require excellent heat resistance and long-term reliability. When a dopant such as CTFE (chlorotrifluoroethylene) is combined with "CYTOP", a non-crystalline, completely fluorinated homopolymer having a $T_g$ of about 108° C., to produce a plastic optical fiber, it functions to greatly lower the $T_g$ of the host polymer. This combination of the dopant and CYTOP reduces the $T_g$ of the final POF to less than 90° C. Since the reduction in $T_g$ decreases time and temperature stability, the use of "CYTOP" is limited in its application to POFs.

Examples of other fluorine-based polymers include Teflon AF (Dupont), a copolymer of 2,2-bistrifluoromethyl-4,5-difluoro-1,3-dioxole and tetrafluoroethylene, represented by the following formula:

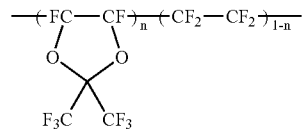

wherein n is a real number of 1 or less.

However, according to a report by the International Plastic Optical Fiber Conference (2001), Teflon AF was reported to have a high optical loss.

In order to effectively produce rod lenses, optical waveguides, optical decouplers, wavelength multiplexers and wavelength demultiplexers, optical attenuators, optical switches, optical isolators, light transmitting modules, light receiving modules, couplers, optical detectors and optical integrated circuits as well as POFs, using optical plastic materials, the optical plastic materials must possess the following properties: they must not exhibit light scattering; they must be substantially transparent over a very broad range of wavelengths; and, they must be excellent in various physiochemical properties including heat resistance. No optical materials satisfying these requirements have hitherto been reported.

There is therefore a need in the art for an optical plastic material that exhibits the following properties: little or no light scattering; substantially transparent in the UV (wavelength: 200~400 nm) and near IR (wavelength: 2,500 nm or shorter) regions; excellent heat resistance, therefore being stable even in the presence of a dopant; and, excellent chemical resistance, moisture resistance and flame retardancy.

The present inventors have earnestly and intensively conducted research to develop an optical plastic material satisfying the above-mentioned requirements. As a result, the present inventors have found that a polymer prepared by the copolymerization of a cyclic perfluoroalkyl vinyl ether having a particular molecular structure and a perfluorinated olefin monomer (for example, tetrafluoroethylene) in a chlorofluorinated organic solvent in the presence of a perfluorinated radical initiator has the following properties: it is substantially transparent in the UV and near IR regions; it has little or no optical loss upon light penetration; it has excellent heat resistance, chemical resistance, moisture resistance and compatibility with conventional dopants; and, it maintains excellent heat resistance even in the presence of a dopant. The refractive index gradient formed by a dopant in the polymer is not deformed despite time passage and varying temperatures and is stably maintained. The present invention is based on these findings.

SUMMARY OF THE INVENTION

Therefore, it is a feature of the present invention to provide a polymer suitable for use in producing an optical plastic material that exhibits the following properties: little or no light scattering and optical loss upon light penetration; substantially transparent at the overall wavelengths; excellent heat resistance, thus being stable even in the presence of a dopant; and, excellent chemical resistance, moisture resistance and flame retardancy.

It is another feature of the present invention to provide an optical plastic material comprising the polymer.

In accordance with the features of the present invention, there is provided a cyclic perfluoroalkyl vinyl ether compound having a particular molecular structure.

In accordance with the features of the present invention, there is further provided a process for preparing a fluorinated polymer by copolymerizing the perfluoroalkyl vinyl ether compound and a perfluorinated olefin monomer in a chlorofluorinated solvent in the presence of a perfluorinated radical initiator.

In accordance with the features of the present invention, there is further provided a polymer prepared by the process.

In accordance with the features of the present invention, there is further provided an optical plastic material comprising the polymer, and optionally a dopant having a refractive index different from the polymer.

In accordance with the features of the present invention, there is further provided a preform for a plastic optical fiber fabricated from the optical plastic material.

In accordance with the features of the present invention, there is yet further provided a plastic optical fiber produced from the preform.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
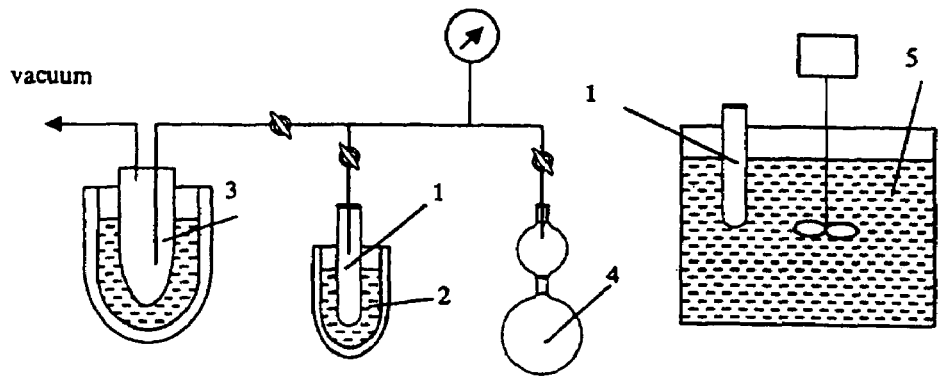
FIGS. 1 and 2 are views schematically showing the structures of polymerization devices usable for the preparation of a polymer in accordance with a preferred embodiment of the present invention.

Hereinafter, the present invention will be explained in more detail with reference to the accompanying drawings.

A cyclic perfluoroalkyl vinyl ether according to the present invention is represented by Formula 1 below:

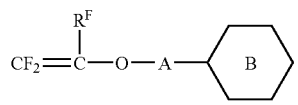

Formula 1 wherein $R^F$ is a fluorine atom or a $C_{1\sim5}$ perfluoroalkyl group; A is a single bond, $-(CF_2)_n-$ (in which n is an integer of 1 to 5) or $-(CF_2CR^F_2-O-CF_2)-$ (in which substituents $R^F$ are each independently a fluorine atom or a $C_{1\sim5}$ perfluoroalkyl group);

is a perfluoro cyclohexyl, perfluorophenyl, perfluorodioxanyl or perfluorodioxalanyl group.

More preferably, the cyclic perfluoroalkyl vinyl ether of the present invention is a compound represented by any one of Formulae 2 to 4 below:

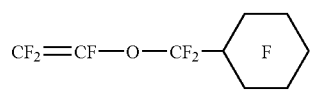

Formula 2

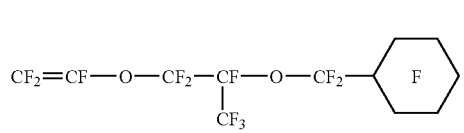

Formula 3

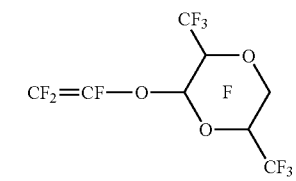

Formula 4

These compounds can be prepared through appropriate pathways by known synthetic processes. For example, the compound of Formula 2 can be prepared by Reaction Scheme 1 below:

Reaction Scheme 1

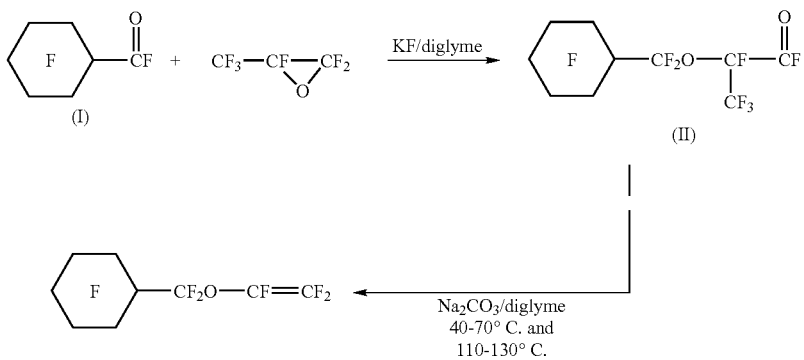

The compound of Formula 4 can be prepared by Reaction Scheme 2 below:

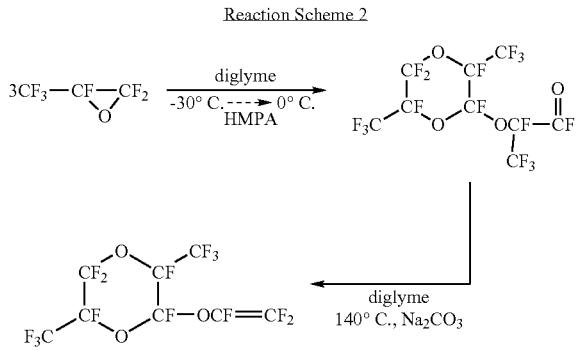

Reaction Scheme 2 wherein HMPA is hexamethylphosphorictriamide ($[(CH_3)_2 N]_3 P=O$)].

The present invention additionally provides a process for preparing a fluorinated polymer by copolymerizing the cyclic perfluoroalkyl vinyl ether and a perfluorinated olefin monomer in a chlorofluorinated solvent in the presence of a perfluorinated radical initiator; and a polymer prepared by the process.

The perfluorinated olefin monomer is preferably a $C_{2~10}$ perfluorinated olefin monomer, and more preferably tetrafluoroethylene (hereinafter, referred to as 'TFE') or hexafluoropropylene. The molar ratio of the cyclic perfluoroalkyl vinyl ether of Formula 1 to the perfluorinated olefin monomer is between 99:1 and 50:50. If the tetrafluoroethylene monomer is used in an amount exceeding 50 mole %, the final polymer has poor amorphousness and heat resistance.

Another fluorinated monomer that can be used in the process of the present invention is represented by Formula 5 below:

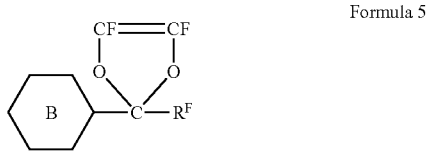

Formula 5 wherein $R^F$ is a fluorine atom or a $C_{1~5}$ perfluoroalkyl group; and

is a perfluoro cyclohexyl, perfluorophenyl, perfluorodioxanyl or perfluorodioxalanyl group.

The perfluorinated radical initiator which can be used in the process of the present invention is preferably a perfluorinated peroxide compound. More preferred radical initiators include bis-perfluorocyclohexylperoxide of Formula 6 below, a polyperfluoroperoxide represented by Formula 7 below and mixtures thereof:

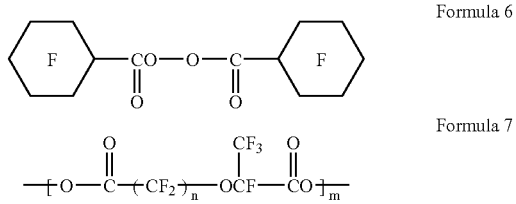

Formula 6

Formula 7 wherein n is an integer between 1 and 10, and m is an integer between 1 and 40.

The molar ratio between the initiator and the total monomers may be suitably selected according to the desired molecular weight of the final polymer and the composition of the monomers. The molar ratio of the total monomers to the initiator is preferably controlled within 10:1~500:1.

The use of the compound of Formula 6 or 7 or a mixture thereof as the initiator is advantageous over the use of conventional initiators in terms of a) good hydrolytic stability in water media, b) a high polymerization rate of the fluorinated monomers at 45~75° C. and c) introduction of a heat resistant terminal group into the polymer.

The polymerization method is not particularly limited. Emulsion polymerization is preferred in that the molecular weight of the polymer can be easily increased to desired levels. On the other hand, one can use chlorofluorinated solvent as a polymerization solvent, preferably 1,2-dichloro-1,1,2,2-tetrafluoroethane.

The polymerization temperature is preferably between 25 and 80° C., but is not particularly limited to this range.

Polymethacrylate has been used as a material for a POF. Since polymethacrylate contains a number of C—H bonds in its chains, stretching or deformation vibration takes place due to the presence of hydrogen atoms in the C—H bonds upon light penetration. As a result, the polymer absorbs light of a particular wavelength and light transmittance is accordingly decreased, which is a main cause of optical loss. That is, when light is irradiated on a material containing C—H bonds, the material absorbs light of a characteristic wavelength corresponding to stretching or resonance vibration of the interatomic bonds.

Accordingly, the material containing C—H bonds is not suitable for use in plastic optical fibers for long-distance communication using light in the near-IR region (600-1550 nm). In order to solve the above problems of the prior art material, the present inventors developed a polymer containing no C—H bonds in the molecular structure. No optical loss therefore takes place by light absorption even at long wavelengths as well as at short wavelengths. The perfluorinated polymer prepared using the cyclic perfluoroalkyl vinyl ether of the present invention can be suitably used as a light transmission medium for optical devices. Light ranging from UV (ultraviolet) (i.e. at wavelengths of 200~400 nm) and near-infrared regions (i.e. at wavelengths of 700~2500 nm) can be used.

Furthermore, since the polymer of the present invention has no functional groups (e.g., carboxyl and carbonyl groups), it has improved heat resistance, moisture resistance, chemical resistance and flame retardancy. Carboxyl groups absorb light in the near-IR region, and carbonyl groups absorb light in the UV region. The removal of such functional groups is therefore advantageous in terms of inhibition of optical loss.

The copolymer prepared using the cyclic perfluoroalkyl vinyl ether of the present invention may be an amorphous polymer. One way to provide such a polymer is by controlling the molar ratio between monomers used. The amorphous polymer inhibits optical loss due to light scattering.

Furthermore, since the polymer of the present invention may have a high molecular weight, a $T_g$ of 190° C. or higher and a thermal decomposition initiation temperature of 270° C. or higher—made by appropriately controlling the composition of monomers—it can be usefully applied to an optical plastic material. For example, a terpolymer prepared from 1 of Formula 2 or 3, monomer 2 of Formula 4, and a tetrafluoroethylene monomer, has a low crystallinity, a high $T_g$, and little or no optical loss even in long wavelength regions.

The present invention also provides an optical plastic material comprising (a) the perfluorinated polymer, and optionally (b) a dopant for providing a refractive index gradient to the final material. Preferably, the dopant has a refractive index difference of 0.001 or more from the perfluorinated polymer.

As noted above, since the polymer prepared by the process of the present invention is transparent over a very broad range of wavelengths, has little or no optical loss upon light penetration, is amorphous and has excellent heat resistance, it can be suitably used as a light transmission medium for optical devices. In particular, since the polymer of the present invention has little optical loss even at long wavelengths as well as at short wavelengths and excellent thermal properties, it can be advantageously used in the production of an SI or GI type plastic optical fiber.

The fabrication of a preform for an SI type plastic optical fiber or the production of an optical fiber by using the polymer of the present invention is possible by any known process. For example, a core is formed from the polymer of the present invention, and a clad is formed from another polymer for an optical fiber having a refractive index different from the polymer of the present invention, thereby obtaining a step refractive index gradient.

Meanwhile, when it is intended to produce a GI-type plastic optical fiber or to fabricate a preform for an optical fiber, a dopant is used for providing a refractive index gradient to the final material. Examples of dopants that can be used in the present invention include any those that can be used to produce a POF, e.g., chlorotrifluoroethylene (CTFE), which has already been used to produce an optical fiber using Cytop by professor Koike. The kind of dopants may be properly selected by considering compatibility with the copolymer, non-volatility and refractive index. In addition, one must take into account that the diffusion during perform fabrication and the separation of the fabricated preform are carried out at a temperature higher than the $T_g$ of the copolymer.

Specific examples of dopants include perfluoro-fluorene, perfluorobenzyltetralin, poly(trifluoro-chloroethylene) oil, perfluoro-polyether oil (Krytox), 1,1,3,5,6-pentachloro-nonafluorobenzene, etc. Perfluoro-polyether oil and perfluorobenzyltetralin are more preferred, and perfluorobenzyltetralin is most preferred. Since perfluorobenzyltetralin is a true solvent for the polymer of the present invention, the diffusion of the dopant becomes easier. Further, since the specific gravity of perfluorobenzyltetralin (2.049 g/cm$^3$) is higher than that of the polymer of the present invention, the dopant is easily diffused into the polymer in the molten state by centrifugal force, thereby facilitating the formation of a refractive index gradient. Any known method can be used to obtain a refractive index gradient by diffusing a dopant into a polymer. A representative method is disclosed in Japanese Patent Laid-open No. Hei 8-334634. The content of a dopant in an optical plastic material can be appropriately determined depending on difference between the refractive index of the polymer and that of the dopant, and a desired refractive index gradient.

The production of an optical plastic material, and particularly, the fabrication of a preform for a GI optical fiber, by using the polymer of the present invention are possible by all common processes. The following process is an example: the amorphous copolymer (a) of the present invention is molded to form a hallow in a reactor; the dopant (b) having a refractive index difference of at least 0.001 from the copolymer (a) is added to the hallow; the reactor is rotated using centrifugal force at a high speed to diffuse the dopant (b) toward the copolymer (a) in a molten state, thereby fabricating a preform for a GI type POF. Since the concentration of the dopant (b) having a relatively high refractive index is higher at the central portion, the preform has a refractive index profile in which the refractive index profile decreases from the center to the peripheral surface.

The polymer prepared by the process of the present invention can be suitably used as a light transmission medium for optical devices such as POFs, optical waveguides, optical decouplers, optical branching filters, optical switches, optical attenuators, optical isolators, optical integrated circuits, light transmitting/receiving modules and the like. The medium is excellent in terms of accessability to the above optical devices, low optical loss and high bandwidth. The GI-type POF produced by using the polymer of the present invention has little or no optical loss, no variation in refractive index gradient depending on time and temperature, and is thus highly stable. Accordingly, the GI type POF produced by using the polymer of the present invention can be advantageously used in various industrial fields, e.g., subscriber communication lines, LANs for public facilities such as factories, hospitals and schools, power line monitoring communication lines, image transmission of monitored operation conditions of automobiles and subways, internal communication of large ocean-going vessels, internal data transmission of aircrafts, picture transmission requiring high speed and high bandwidth in commercial game sets, transmission of high definition children's stories and 3-dimensional pictures, wires of devices such as computers or automatic switches, general indoor communication networks, various sensors and the like.

EXAMPLES

Hereinafter, the present invention will be described in more detail with reference to the following preferred examples. However, these examples are given for the purpose of illustration and are not to be construed as limiting the scope of the invention.

Synthesis of Monomers

1) Synthesis of FM 1:

As depicted in the reaction scheme below, hexafluoropropyleneoxide was added to a mixture of compound (I) (fluoroketone of perfluorocyclohexane carboxylic acid) and diglyme (dimethylether of diethylene glycol) in a glass reactor at 0° C., and reacted to obtain compound (II) (b.p: 135° C.). The conversion rate of the compound (I) was 50%, and the yield of the compound (II) was 37%.

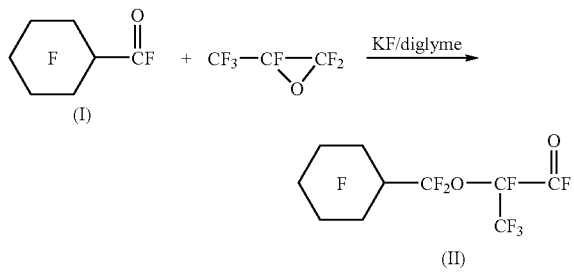

Na$_2$CO$_3$ and diglyme were added to a mixture containing the compound (II) and reacted at 50° C. The reaction mixture was heated to 120° C., and further reacted to give a reaction mixture containing monomer FM-1 (conversion rate of compound (II): 100%):

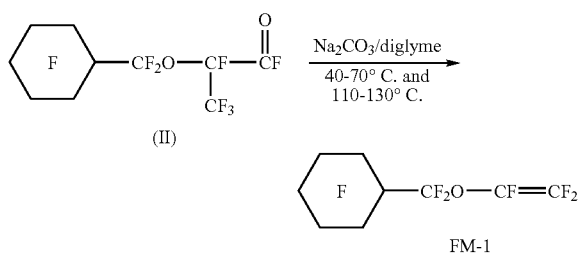

The monomer FM-1 was separated from the reaction mixture at reduced pressure, washed with water to remove the diglyme, dried over calcined magnesium sulfate, and purified using a Perkin Elmer rectification column to give pure monomer FM-1 of the following formula (yield: 75%).

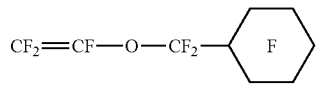

The monomer FM-1 was observed to have a boiling point of 122° C.

2) Synthesis of FM 1a:

The compound (II) and hexafluoropropyleneoxide were subjected to condensation to give compound (III) of the following formula:

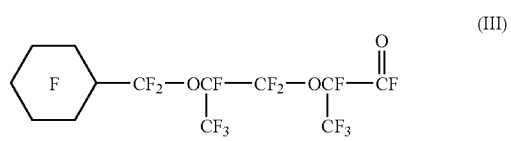

Similarly to the synthesis of FM-1, Na$_2$CO$_3$ and diglyme were added to the compound (III) and reacted to obtain monomer FM-1a of the following formula:

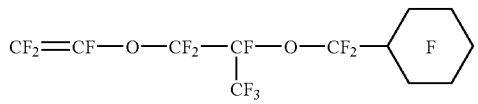

3) Synthesis of Monomer FM-2:

Monomer FM-2 was synthesized in accordance with the following reaction scheme:

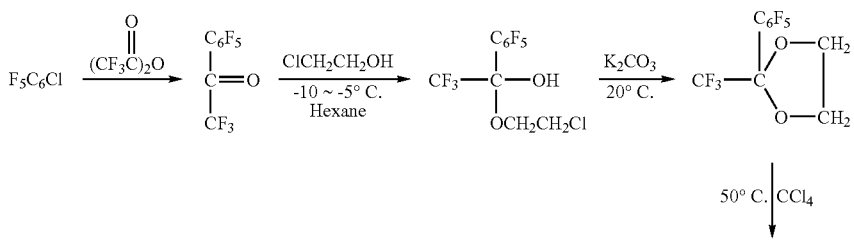
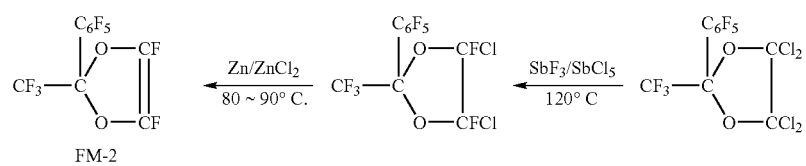

In step 1, pentafluorophenylchloride and trifluoroacetic anhydride were reacted to obtain octafluoroacetophenone. In steps 2 and 3, the octafluoroacetophenone was reacted with chloroethanol in hexane at −10~−5° C. The reaction product was reacted with dry $K_2CO_3$ at 20° C. for 6 hours to obtain 2-trifluoromethyl-2-pentafluorophenyl-1,3-dioxalane in a yield of 80%. In step 4, the fluoro-containing dioxalane was chlorinated with carbon tetrachloride at 50° C. to obtain 2-trifluoromethyl-2-pentafluorophenyl-4,4,5,5,-tetrachloro-1,3-dioxalane (yield: 95%) as a colorless crystal. The product was measured to have a melting point of 41~42° C. and a boiling point of 140~141° C./40 mmHg. In step 5, the dioxalane obtained in step 4 was chlorinated with $SbF_3/SbCl_5$ at 120° C. for 2.5 hours to obtain a reaction mixture containing fluorinated dioxalane. The reaction mixture was subjected to rectification to give 2-trifluoromethyl-2-pentafluorophenyl-4,5-dichloro-4,5-difluoro-1,3-dioxalane in a yield of 70%. The analytical data of the NMR spectrum of the product are as follows:

NMR $^{19}F$ ($CH_3Cl$) δ m.g.: −159.6, 159.3(s) ($F^2$, 2F), −146.73($F^3$, 2F), −135.98(m) ($F^1$, 2F), −84.61, −84.16(t), −67.54(m), −65.74(s), −58.67, −54.01(m)

In step 6, the difluorinated derivative of dioxalane was dehalogenated in N-methylpyrrolidone with the aid of Zn and $ZnCl_2$ at 90° C. to give monomer FM-2.

In the IR spectrum, the monomer FM-2 had a carbon-carbon double bond band at 1885 cm$^{-1}$. The boiling point of the monomer FM-2 was measured to be 86° C./38 mmHg.

4) Synthesis of FM-3:

As depicted in the following reaction scheme, 3,6-perfluorodimethyl-1,4-dioxanyl-5-vinyl ether (hereinafter, referred to as 'monomer FM-3') was synthesized.

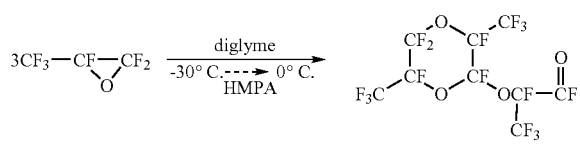

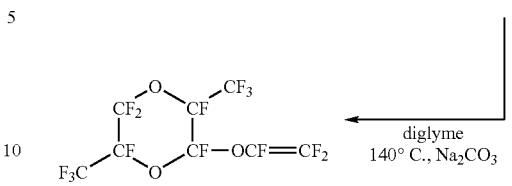

GC and NMR $^{19}F$ analyses indicate that the monomer FM-3 has three isomers. The boiling point of the monomer FM-3 was measured to be 103~105° C., the content of the major isomer in the monomer FM-3 was shown to be 98%, and the yield of the monomer FM-3 was shown to be 80%.

Synthesis of Initiators

1) Synthesis of DAP-1

Bis-perfluorocyclohexanoylperoxide was synthesized in accordance with the following reaction scheme:

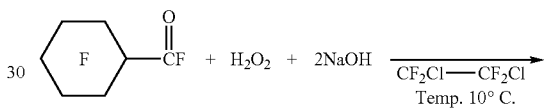

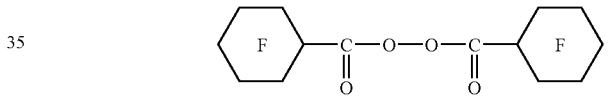

The reaction was conducted in $CF_2Cl$—$CF_2Cl$ (1,2 dichloro-1,1,2,2-tetrafluoroethane: hereinafter, referred to as 'R113') at 10° C. Peroxide was separated from the aqueous layer, and dried over anhydrous sodium sulfate. The final yield was 90%. The obtained peroxide was stored in a 10~20% R113 solution.

The main characteristics of the bis-perfluorocyclohexanoylperoxide are shown in the following table:

| Formula | Molecular weight | NMR F$^{19}$ No. singlet | $T_{melting}$ ° C. |
|---|---|---|---|
| ![structure] | 650 | 1,5<br>2,4<br>3<br>6 | 40.1~40.3 |

2) Synthesis of DAP-2

In order to obtain a perfluoroperoxide initiator which enables polymerization around room temperature and introduction of the group —$CF_2(CF_3)$—O—CF— into a polymer backbone, hexafluoropropyleneoxide and difluoroanhydride of octafluoroadipic acid (I) were subjected to condensation to give a diacylpolyperfluoroperoxide initiator (DAP-2). The reaction scheme is as follows:

have a low molecular weight. The homopolymer was in the form of a viscous gel at 20° C.

3) Homopolymerization of FM-3:

Homopolymerization of FM-3 was performed under the same polymerization conditions as the homopolymerization of FM-1 to give a homopolymer of FM-3. The yield of the homopolymer was 14%. The homopolymer was completely amorphous in the form of a transparent jelly.

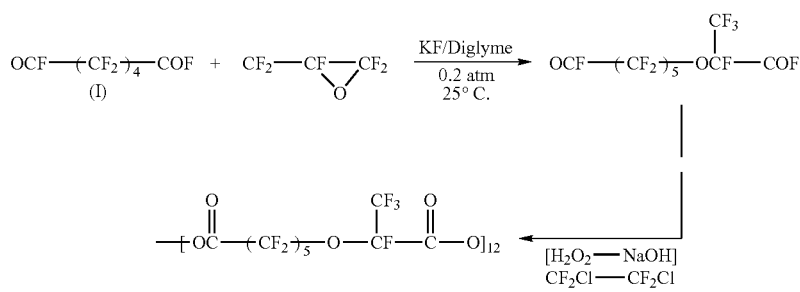

The characteristics of the peroxide are shown in the following table:

| Peroxide | Half life τ (hrs) at T° C. | | Yield (□) |
|---|---|---|---|
| | 30.0° C. | 35.0° C. | |
| DAP-2 | 2.7 | 1.6 | 60 |

Preparation of Polymers

Figure 2:
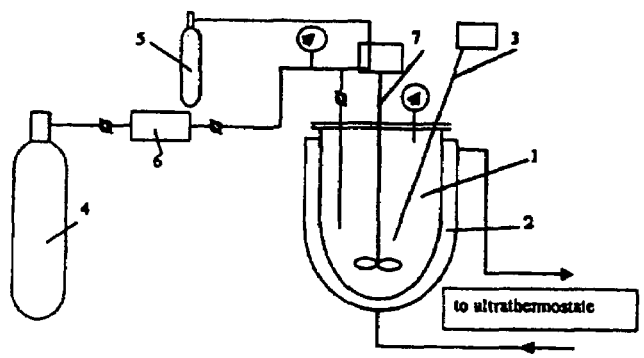

Using the polymerization devices shown in FIGS. 1 and 2, homopolymerization and copolymerization were performed.

The homopolymerization was performed in a 200 ml glass ampoule (FIG. 1), and the copolymerization of the monomer and tetrafluoroethylene was performed in a steel ampoule equipped with a mechanical agitator (FIG. 2).

Radical polymerization was performed in R113 at 25~60° C. in the presence of DAP-1 or DAP-2 as an initiator. Oxygen in air was removed from the reaction medium at −196° C. The obtained polymer was separated using alcohol, centrifuged, and dried at 120° C. until the weight was maintained to be constant.

Hereinafter, the homopolymerization, the copolymerization and the characteristics of the obtained polymers will be described.

1) Homopolymerization of FM-1:

DAP 1 was used as an initiator, and the molar ratio of the monomer to the initiator (FM-1: DAP-1) was controlled to 60:1. FM-1 was subjected to homopolymerization for 5~6 hours to give a homopolymer of FM-1. The yield of the homopolymer was 20%, and the weight average molecular weight was measured to be 8,500. The homopolymer was transparent at 20° C.

2) Homopolymerization of FM-1a:

Homopolymerization of FM-1a was performed under the same polymerization conditions as the homopolymerization of FM-1 to give a homopolymer of FM-1a. The yield of the homopolymer was 15%. The homopolymer was shown to 4) Copolymerization of FM-1 and Tetrafluoroethylene (Hereinafter Referred to as 'TFE'):

Copolymerization was performed in R113 at 2.5 atm and 60° C. for 2 hours in the presence of DAP-1 as an initiator. The molar ratio of the total monomers to the initiator ((FM-1+TFE):DAP-1) was controlled to 190:1, and the molar ratio of FM-1 to TFE was controlled to 65:35. The yield of the copolymer was 80%. The copolymer was in the form of a solid light powder, and was measured to have a molecular weight 10~100 times higher than that of the homopolymer of FM-1. The copolymer contained 5% or more crystalline region. As the molar fraction of TFE was increased, the crystalline region (%) was increased. The copolymer was measured to have a boiling point of 200° C., and a thermal decomposition initiation temperature of 270° C.

5) Copolymerization of FM-1a and TFE:

A copolymer (yield: 70%) of FM-1a and TFE was prepared in the same manner as in 4) above, except that the molar ratio of the total monomers to the initiator (FM-1a+TFE):DAP-1 was changed to 190:1, and the molar ratio of the FM-1a to TFE was changed to 65:35. The copolymer contained a slightly crystalline phase.

6) Copolymerization of FM-3 and TFE:

A copolymer (yield: 35%) of FM-3 and TFE was prepared in the same manner as in 4) above, except that the molar ratio of the total monomers to the initiator (FM-3+TFE):DAP-1 was changed to 190:1, and the molar ratio of the FM-3 to TFE was changed to 65:35. The copolymer was in the form of a solid and contained a minimal crystalline phase. The $T_g$ was measured to be 192° C.

7) Terpolymer of FM-1, FM-3 and TFE:

DAP-2 was used as an initiator, the molar ratio of the total monomers to the initiator was 190:1, the molar ratio between the monomers (FM-1:FM-3:TFE) was 4:4:2, and copolymerization was performed at 25° C. for 2 hours. The yield of the terpolymer was 52%. The terpolymer contained a minimal crystalline phase. The terpolymer had a $T_g$ of 172° C.

Fabrication of Preform 1 for GI Type POF 50 g of the copolymer prepared in 4) above was charged into a glass tube (diameter: 4 cm), and rotated in the vertical position at a rate of 6,000 rpm and 270° C. for 6 hours to form a hallow in the tube. Perfluorobenzyltetralin (25 wt %) as a dopant was filled into the hallow and rotated in the vertical position at a rate of 4,000 rpm and 200~220° C. for 8 hours. At this time, the dopant was diffused into the copolymer due to a difference between the specific gravity of the dopant and that of the copolymer to form a refractive index gradient. The resulting preform was cooled to room temperature to fabricate a final preform (diameter: 4 cm) for a GI type plastic optical fiber. The difference between the refractive index of the central portion and that of the peripheral surface was confirmed to be 0.01.

Fabrication of Preform 2 for GI Type POF 50 g of the copolymer prepared in 5) above was charged into a glass tube (diameter: 4 cm), and rotated in the vertical position at a rate of 5,000 rpm and 270° C. for 5 hours to form a hallow in the tube. Perfluorobenzyltetralin (25 wt %) as a dopant was filled into the hallow and rotated in the vertical position at a rate of 4,000 rpm and 200~220° C. for 7 hours. At this time, the dopant was diffused into the copolymer due to a difference between the specific gravity of the dopant and that of the copolymer to form a refractive index gradient. The resulting preform was cooled to room temperature to fabricate a final preform (diameter: 4 cm) for a GI type plastic optical fiber. The difference between the refractive index of the central portion and that of the peripheral surface was confirmed to be 0.015.

Fabrication of Preform 3 for GI Type POF 50 g of the copolymer prepared in 6) above was charged into a glass tube (diameter: 4 cm), and rotated in the vertical position at a rate of 6,000 rpm and 270° C. for 5 hours to form a hallow in the tube. Perfluorobenzyltetralin (25 wt %) as a dopant was filled into the hallow and rotated in the vertical position at a rate of 4,000 rpm and 200~220° C. for 7 hours. At this time, the dopant was diffused into the copolymer due to a difference between the specific gravity of the dopant and that of the copolymer to form a refractive index gradient. The resulting preform was cooled to room temperature to fabricate a final preform (diameter: 4 cm) for a GI type plastic optical fiber. The difference between the refractive index of the central portion and that of the peripheral surface was confirmed to be 0.015.

Fabrication of Preform 4 for GI Type POF 50 g of the copolymer prepared in 7) above was charged into a glass tube (diameter: 4 cm), and rotated in the vertical position at a rate of 6,000 rpm and 270° C. for 5 hours to form a hallow in the tube. Perfluorobenzyltetralin (25 wt %) as a dopant was filled into the hallow and rotated in the vertical position at a rate of 4,000 rpm and 200~220° C. for 7 hours. At this time, the dopant was diffused into the copolymer due to a difference between the specific gravity of the dopant and that of the copolymer to form a refractive index gradient. The resulting preform was cooled to room temperature to fabricate a final preform (diameter: 4 cm) for a GI type plastic optical fiber. The difference between the refractive index of the central portion and that of the peripheral surface was confirmed to be 0.017.

Measurement of Refractive Index Gradients:

The refractive index gradient of the preforms 1 to 4 fabricated above was measured in accordance with the following procedure. The results are summarized in Table 1 below.

1) Method: Confocal Raman Spectroscopy

2) A 20 mW helium-neon laser (632.8 nm) was used. The Raman scattering spectroscopy shows the results measured using an Olympus BH microscope when pinholes were set to 50 μm.

According to how parabolic the refractive index of the preforms was changed toward the peripheral surface, the most parabolic form was judged to be "excellent", and the relatively parabolic form was judged to be "good".

TABLE 1

| Preform for POF | Dopant content (wt %) | Diffusion time (hr) | Diffusion temp. (° C.) | Average $T_g$ of Preform (° C.) | Degree of refractive index gradient of preform |
|---|---|---|---|---|---|
| 1 | 25 | 8 | 200-220 | 120 | Excellent |
| 2 | 25 | 7 | 200-220 | 121 | Good |
| 3 | 25 | 7 | 200-220 | 110 | Good |
| 4 | 25 | 7 | 200-220 | 130 | Good |

Figure 3:
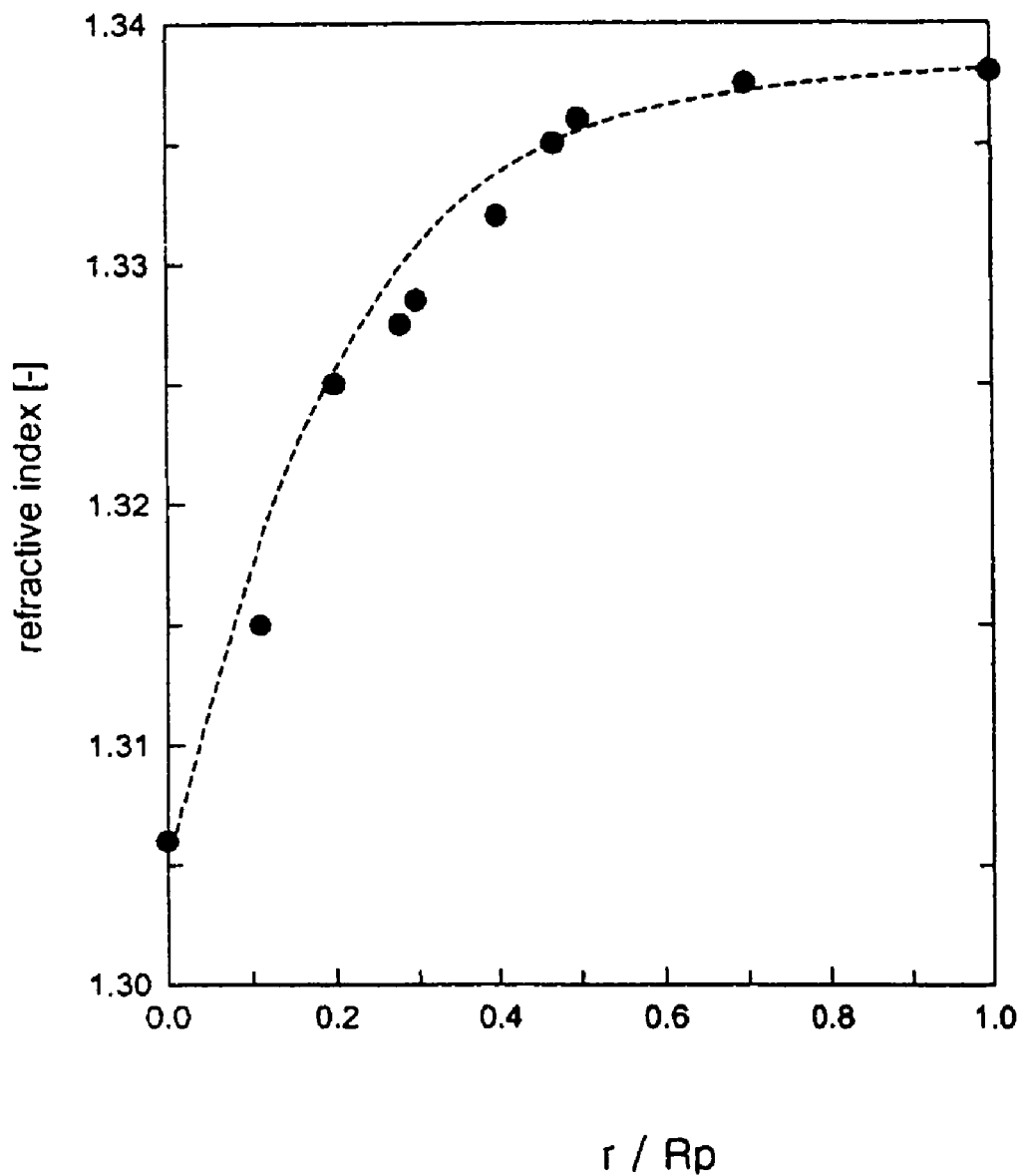
FIG. 3 is a graph showing the refractive index gradient of a preform for a GI type plastic optical fiber according to a preferred embodiment of the present invention.

The refractive index gradient of the preform 1 for an optical fiber is shown in FIG. 3. As can be seen from FIG. 3, the refractive index gradient of the preform is parabolic.

As apparent from the above description, the polymer prepared by the copolymerization of the cyclic perfluoroalkyl vinyl ether of the present invention has a high molecular weight, is substantially transparent in the UV and near IR regions, and can be completely amorphous by controlling the molar ratio between monomers. Accordingly, the copolymer of the present invention can be usefully applied to an optical plastic material. In particular, the preform for a GI-type plastic optical fiber fabricated by using the copolymer of the present invention has a high $T_g$, a parabolic refractive index profile, superior thermal stability and little or no optical loss.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A perfluoroalkyl vinyl ether compound represented by Formula 1 below:

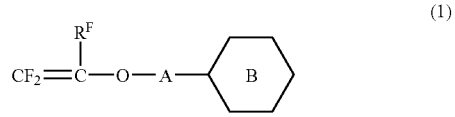

(1)

wherein $R^F$ is a $C_{1-5}$ perfluoroalkyl group; A is —$(CF_2)_n$— in which n is an integer of 2 to 5, or —$(CF_2CR^F_2$—O—$CF_2)$— in which the substituents $R^F$ are each independently a fluorine atom or a $C_5$ perfluoroalkyl group;

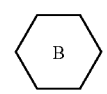

is a perfluorophenyl group.

* * * * *